(12) United States Patent
Dittgen et al.

(10) Patent No.: US 6,303,137 B1
(45) Date of Patent: Oct. 16, 2001

(54) INJECTABLE IMPLANT

(75) Inventors: Michael Dittgen, Apolda; Sabine Fricke, Jena; Hagen Gerecke, Jena; Ines-Patricia Möller, Jena; Christoph Völkel, Jena, all of (DE)

(73) Assignee: Jenapharm GmbH & Co. KG, Jena (DE)

( * ) Notice: Subject to any disclaimer, the term of this patent is extended or adjusted under 35 U.S.C. 154(b) by 0 days.

(21) Appl. No.: 09/341,206

(22) PCT Filed: Dec. 3, 1997

(86) PCT No.: PCT/DE97/02903

§ 371 Date: Aug. 16, 1999

§ 102(e) Date: Aug. 16, 1999

(87) PCT Pub. No.: WO98/30245

PCT Pub. Date: Jul. 16, 1998

(30) Foreign Application Priority Data

Jan. 10, 1997 (DE) .............................. 197 01 912

(51) Int. Cl.[7] .............................. A61F 2/02; A61K 47/30
(52) U.S. Cl. ......................................... 424/426; 514/772.3
(58) Field of Search .......................... 424/426; 514/772.3

(56) References Cited

FOREIGN PATENT DOCUMENTS

| 19701912 | 5/1998 | (DE) . |
| 8600533 | 1/1986 | (WO) . |
| 8804557 | 6/1988 | (WO) . |
| 9003768 | 4/1990 | (WO) . |
| 9535093 | 12/1995 | (WO) . |

OTHER PUBLICATIONS

Jeong B. et al, "Biodegradable block copolymers as injectable drug–delivery systems", Nature, 1997, 388/6645 (860–862).

Miyamoto S. et al, "Polylactic acid–polyethylene glycol block copolymer. A new biodegradable synthetic carrier for bone morphogenetic protein.", Clin Orthop, Sep. 1993, (294) p. 333–43.

Ha J.–H et al, "Albumin release from bioerodible hydrogels based on semi–interpenetrating polymer networks composed of poly(epsilon–caprolactone) and poly(ethylene glycol) macromer", Journal of Controlled Release, Bd. 49, Nr. 2–3, Dec. 1997.

Schmidmaier G. et al, "A new biodegradable polylactic acid coronary stent–coating, releasing PEG–Hirudin and prostacycline analog, reduces both platelet activiation and plasmatic coagulation", Journal of the American College of Cardiology, 29 (2 Suppl. A), 1997, 354A.

Van Der Giessen W.J. et al, Marked inflammatory sequelae to implantation of biodegradable and nonbiodegradable polymers in porcine coronary arteries:, Circulation, 1997, 94/7 (1690–1697).

Bhardwaj R. et al, "In vitro evaulation of Poly (d,l–lactide–co–glycolide) polymer–based implants containing the alpha–melanocyte stimulating hormone analog, Melanotan–I", Journal of Controlled Release, Bd. 45, Nr. 1, 3 Mach 1997.

*Primary Examiner*—Carlos Azpuru
(74) *Attorney, Agent, or Firm*—Wood, Phillips, VanSanten, Clark & Mortimer

(57) ABSTRACT

This invention relates to an in-situ implant that can be produced by placing a sterile, injectable, and water-insoluble complex from a biodegradable polymer and a biocompatible polyether with functional end-groups in the organism, and coagulating them under the influence of the body fluid. This coagulate may optionally contain at least one bioactive substance selected from the group of hormones, immunomodulators, immunosuppressants, antibiotics, cytostatics, diuretics, gastro-intestinal agents, analgesics, local anaesthetics and/or neuropharmacological agents.

12 Claims, 5 Drawing Sheets

INJECTABLE IMPLANT

CROSS-REFERENCES TO RELATED APPLICATIONS

This application is the national phase application (under 35 U.S.C. §371) of PCT/DE97/02903 Dec. 3, 1997 and is related to foreign application 197 01 912.9 Jan. 10, 1997 (FED REP GERMANY).

STATEMENT REGARDING FEDERALLY SPONSORED RESEARCH AND DEVELOPMENT

Not applicable.

REFERENCE TO A "MICROFICHE APPENDIX"

Not applicable.

1. Field of Invention

This invention relates to an in-situ implant that can be produced by placing a sterile, injectable, and water-insoluble complex from a biodegradable polymer and a biocompatable polyether with functional end-groups in the organism, and coagulating them under the influence of the body fluid.

2. Description of the Related Art

Known implants for applying bioactive substances consist of microparticles or are produced by pressing under aseptic conditions. The commercial preparation Zoladex® is an example of a pressed implant. This implant causes considerable pain at the place of application. Similar disadvantages can be found with th epreparatoins injected in the form of microparticles such as Parlodel®, Profact® Depot, Enantone®-Gyn one-month depot, and Decapeptyle Gyn.

The most common manufacturing process for microparticles or microspheres is the solvent evaporation technique that uses organic solvents that are toxic for the living organism.

The solvent evaporation technique uses an emulsion of a biodegradable polymer from which the solvent is gradually removed. Suitable solvents such as methylene chloride [Hora, M. S. et al., Bio/Technology 8(1990), pp. 755–758; Bodmeier, R. et al., Pharm. Res. 12 (8/1995), pp. 1211–1217; Lu, W. Q. et al., Biotechn. Prog. 11 (2/1995), pp. 224–227; Cohen, S. et al., Pharm. Res. 6 (8/1991), pp. 713–720], mixtures of methylene chloride and methanol [Mehta, R. C. et al., J. Contr. Rel. 29 (1994), pp. 375–384], dichloromethane [Kissel, T. et al., J. Contr. Rel. 39 (1996), pp. 315–326], or chloroform [Hayashi, Y. et al., Pharm. Res. 11 (2/1994), pp. 337–340] are at least physiologically risky. The biodegradable polymer is also dissolved in solvents such as methylene chloride when the spray drying method is used [Bodmeier, R. et al., Pharm. Res. 12 (8/1995), pp. 1211–1217] and subsequently converted into the solid form with the bioactive substance in a spray process. A joint disadvantage of both manufacturing processes for microparticles is their content of residual solvent. In addition, the spray drying method requires a large amount of chemical engineering equipment.

U.S. Pat. No. 4,938,763 describes the manufacturing of implants formed in situ. The process described therein starts with dissolving biodegradable polymers such as polylactides and polylactide co-glycolides in a solvent. This solution is injected. When it comes into contact with body fluid, a solid implant is formed that consists of the precipitated biodegradable polymer and the bioactive substance while the solvent completely leaves the implant and is dissipated in the organism. Solvents named are ethanol, propylene glycol, ketones, and others. A disadvantage of this method, however, is that the solvents listed are physiologically active and can therefore be applied parenterally to a limited extent only. Furthermore, a method for producing implants formed in situ is described according to which a solution of monomers or oligomers (prepolymers) is injected with an admixture of starter substances and/or catalysts. After the injection the ingredients become a biodegradable polymer. With this method, highly reactive substances have to be used to start polymerization, and these are toxic.

According to Eliaz et al. [Proc. 3rd Jerusalem Conference to Pharmaceutical Sciences and Clinical Pharmacology, Sep. 1–6, 1996] the same method can be used to produce an implant formed in situ if glycofurol is used as low-molecular solvent for homo- and copolymers of polylactic acid. The implants produced in this way are particularly suited for proteins. The protein-containing solutions are low-viscous and can be injected easily. Glycofurol can be mixed with water and is physiologically relatively harmless.

During the process of in-situ forming, the glycofurol is immediately drained off with the watery environment. This can have an adverse effect on the release of the active ingredient from the implant. Studies have confirmed this result.

U.S. Pat. No. 3,887,699 describes a method for producing implants for subcutaneous application which consists in forming formed balls on the basis of polylactic acid homopolymers or copolymers with glycolic acid of a sufficiently high molecular weight and an active ingredient. The integrity of the balls produced is retained for a long period after implanting, and release of the active ingredient is delayed. Suitable active ingredients mentioned are steroids that act as contraceptives.

A major disadvantage of these particles containing active ingredients is their production using the solvent evaporation method and organic solvents (chloroform). The risks that residual solvents hold were mentioned above.

U.S. Pat. No. 3,773,919 describes a similar method. It says that pharmaceutic depot formulations that release adequate quantities of active ingredient parenterally and in a controlled way can be produced easily if the depot of active ingredient is greater than an individual dose and if there is a homogeneous mixture of polylactic acid and active ingredient at a ratio of 1 to 99 each. The active ingredient in this case should be an substance acting on the endocrine system or a fertility-controlling substance.

It is a disadvantage of this method that the solid particles have to be suspended in a saline solution or in a pharmaceutically suitable oil before they can be injected. Homogeneity problems of these suspensions have to be expected.

WO-9517901 describes a cytostatic composition that can be injected into lesions. It contains the cytostatic in a matrix consisting of a fatty acid that cannot be mixed with water.

This composition has the benefit that it is flowable to an extent that it can be injected. But the extended action of the cytostatic is caused by the viscosity of the matrix. The viscosity of the matrix, however, is an unreliable parameter as it may vary depending on the quantity of body fluid available. It is further known that fatty acids are biocompatible to a limited extent only and may damage the tissue.

WO-9103491 describes a matrix based on protein that is to effectively inhibit cell proliferation. It either contains a collagen or a fibrinogen.

This matrix requires smaller quantities of protein as compared to conventional systems. The disadvantages of this invention are that the release of the active ingredient cannot be controlled by the composition of the matrix, and that a vasoconstrictor is required for retardation.

EP-0341007 refers to a method for producing an adhesive formed in situ that coagulates with the wound plasma by contacting the collagen-containing agent.

The advantage of this method is that it acts immediately after administration by forming the coagulate that results in wound closure. This technique, however, can only be applied to dermal preparations during and after surgery and does not include the incorporation of active ingredients.

EP-0328389 describes a method of injecting a macromolecular matrix using vinca alkaloids for the treatment of intracranial tumors.

The macromolecular matrix on a protein base enhances the drift of the alkaloid away from the injury, thereby ensuring high levels of local efficacy. It is disadvantageous, however, that a vasodilator has to be added for this effect, so that control of local efficacy remains to be a problem.

A similar situation is found in WO-8902734. This invention deals with a pharmaceutical vehicle that administers vasoconstrictors and cytotoxically acting substances for the treatment of neoplastic injuries.

This vehicle, however, requires modifiers that modify the cell structure to change cell permeability.

According to U.S. Pat. No. 4,619,913 a collagen- or fibrinogen-containing matrix can be produced that forms an amorphous flowable mass in an aqueous medium which enables the treatment of neoplastic injuries or the surrounding tissue.

This technique is to prevent the active ingredient from being transported to undesired regions and to achieve an increased therapeutic effect. At the same time, the active ingredient is protected against metabolic deactivation. The method holds clear advantages with tumors that cannot be treated by surgery or radiotherapy. Collagens are not harmless in immunological respect and can cause undesirable reactions of the organism.

EP-167263 describes the same method for producing a polymer matrix containing a cytotoxic agent which it slowly releases to prevent undesirable systemic effects.

This method reduces cytotoxic side-effects to a large extent. Here again, application is combined with administering a vasoconstrictor that is to prevent the drain-off of the active agent with the bloodstream or lymph flow. Its disadvantages have been pointed out above.

U.S. Pat. No. 5,290,552 describes an adhesive matrix to be used for closing wounds after surgical operations. It coagulates in a pH range around 5 and is therefore well-suited for treating dermal injuries.

But this matrix is unsuitable for parenteral administration as the pH values of the body fluids do not bring about the desired coagulation of the matrix.

It is the problem of the present invention to provide an injectable implant that overcomes the disadvantages of the state of the art.

DETAILED DESCRIPTION OF THE INVENTION

This problem is solved according to the invention in that an in-situ implant is provided that can be produced by placing a sterile, injectable, and water-insoluble complex from a biodegradable polymer and a biocompatible polyether with functional end-groups in the organism, and coagulating them under the influence of the body fluid.

In a study of a great number of biocompatible complexing agents it was found, surprisingly, that polyethers with functional end-groups and defined structures are in a narrow range of concentrations capable of forming sterile injectable water-insoluble complexes with biodegradable polymers selected from the group of poly($\alpha$-hydroxy) esters and their copolymers.

Therefore, implants are preferred wherein the biodegradable polymer is a compound from the group of poly($\alpha$-hydroxy-ester) or its copolymers.

Also preferred are implants wherein the biocompatible polyether with functional end-groups is a compound of the general formula I

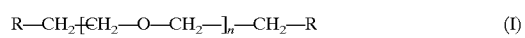  (I)

where

R represents —OH, —CH$_2$OH, —CH$_2$CH$_2$OH or their homologs, n is an integer from 4 to 12, and the relative molar mass of the compound of the general formula I is 200 to 600 mass units.

Particularly preferred are implants wherein R represents —OH.

Preferred implants have a ratio of biodegradable polymer to polyether of 1:100 and 1:2, particularly preferred are ratios in the range from 1:6 and 1:3.

The complexes according to the invention thus contain just the biocompatible polymers listed above and are applied without adding starter substances or catalysts.

The implants of the invention can contain bioactive substances. In preferred implants, the coagulate contains at least one bioactive substance selected, for example, from the group of hormones, immunomodulators, immunosuppressants, antibiotics, cytostatics, diuretics, gastro-intestinal agents, cardiovascular agents, anti-inflammatory agents, analgesics, local anaesthetics and/or neuropharmacological agents.

The suitable polyethers with functional end-groups have the general formula I

  (I)

where R=OH, CH$_2$OH, CH$_3$CH$_2$OH etc., best suited and preferred are polyethers where R=OH, M=200 . . . 600, and n=4 . . . 12. These are named as listed in Table 1 below.

TABLE 1

| Abbreviations of polyethers with functional end-groups | |
|---|---|
| PE 1 | Polyether where R = –OH, M = 200, n = 4 |
| PE 2 | Polyether where R = –OH, M = 400, n = 8 |
| PE 3 | Polyether where R = –OH, M = 600, n = 12 |

The desired sterile injectable water-insoluble complexes only form at suitable concentration rations of the biodegradable polymer and the polyether with functional end-groups (Table 2).

TABLE 2

Injectability/coagulate formation of the complexes of biodegradable polymer/PE

| biodegradable Polymer | PE | 0% | 1% | 5% | 10% | 15% | 20% | 25% | 30% | 35% |
|---|---|---|---|---|---|---|---|---|---|---|
| RG 503 | PE 1 | +/- | +/+ | +/+ | +/+ | - | - | - | - | - |
|  | PE 2 | +/- | +/+ | +/+ | +/+ | +/+ | +/+ | +/+ | +/+ | - |
|  | PE 3 | +/- | +/+ | +/+ | +/+ | +/+ | +/+ | - | - | - |
| RG 503 H | PE 1 | +/- | +/+ | +/+ | +/+ | - | - | - | - | - |
|  | PE 2 | +/- | +/+ | +/+ | +/+ | +/+ | +/+ | - | - | - |
|  | PE 3 | +/- | +/+ | +/+ | +/+ | +/+ | +/+ | - | - | - |
| RG 752 | PE 1 | +/- | +/+ | +/+ | +/+ | - | - | - | - | - |
|  | PE 2 | +/- | +/+ | +/+ | +/+ | +/+ | +/+ | - | - | - |
|  | PE 3 | +/- | +/+ | +/+ | +/+ | +/+ | +/+ | - | - | - |
| RG 858 | PE 1 | +/- | +/+ | +/+ | +/+ | +/+ | +/+ | - | - | - |
|  | PE 2 | +/- | +/+ | +/+ | +/+ | +/+ | +/+ | - | - | - |
|  | PE 3 | +/- | +/+ | +/+ | +/+ | +/+ | +/+ | - | - | - |
| L 104 | PE 1 | +/- | +/+ | +/+ | +/+ | +/+ | +/+ | - | - | - |
|  | PE 2 | +/- | +/+ | +/+ | +/+ | +/+ | +/+ | - | - | - |
|  | PE 3 | +/- | +/+ | +/+ | +/+ | +/+ | +/+ | - | - | - |

Legend:
PE = polyether with functional end-groups
+/- = injectable/no coagulate
+/+ = injectable/coagulate
- = not injectable
RG, L = Boehringer Ingelheim polylactide-co-glycolide For RG 503 polylactide-co-glycolide, the optimum range of concentration for PE 1 is between 1 and 10%, for PE 2 between 1 and 30%, and for PE 3 between 1 and 20%. For RG 503 H and RG 752 polylactide-co-glycolide, the optimum range of concentration for PE 1 is between 1 and 10%, for PE 2 and PE 3 between 1 and 20%. For RG 858 polylactide-co-glycolide and the L 104 polylactide, the optimum range of concentration for PE 1,2 and 3 is between 1 and 20%.

The complexes are sufficiently flowable at the optimum ranges of concentration given above to be injected painlessly. The complexes allow conventional sterilizing methods, especially thermal processes. They can carry bioactive substances selected from the group of hormones, immunomodulators, immunosuppressants, antibiotics, cytostatics, diuretics, gastro-intestinal agents, cardiovascular agents, anti-inflammatory agents, analgesics, local anaesthetics and/or neuropharmacological agents.

Among the active ingredients that are suited for these applications are testosterone and its esters, estradiol, progesterone, gonadoliberin analogs, prostaglandins and their derivatives, cyclosporin, cortison, prednisolon, dexamethasone, penicillin derivatives, cephalosporin derivatives, macrolide antibiotics, polypeptide antibiotics, proteins of the interleukin and interferon groups, aciclovir, cyclophosphamide, methotrexate, zidovudine, misoprostol, furosemide, amiloride, nitroglycerin, nifedipine, verapamil, haloperidol, amitryptiline, piroxicam, ibuprofen, indomethacin, diclofenac, morphine, pethidine, naloxone, tetracaine, lidocaine.

A coagulate is formed under the influence of body fluids after placement in the organism. The biological decomposition of this coagulate which may take any time from weeks and months (RG series Boehringer Ingelheim manufacturer's information) or months and years (L series Boehringer Ingelheim manufacturer's information) is accompanied by the release of the active ingredient.

It is therefore preferred to control the release of the bioactive substance by components of the sterile injectable water-insoluble complex. It is therefore possible to adjust the release rate to the pharmacokinetics and pharmacodynamics of the active ingredients in the organism.

The injectable complexes are preferably sterilized to form implants. This sterilization can be achieved by a known thermal process or by aseptic practice, or a combination of such methods.

An object of this invention further is a method for producing an implant according to the invention wherein a sterile injectable water-insoluble complex of a biodegradable polymer and a biocompatible polyether with functional end-groups is placed in the organism, and coagulated under the influence of body fluid.

The invention shall be explained in greater detail using the examples below.

Testing Method

Release of the bioactive substances (testosterone, progesterone, interleukin-2) was tested in a release apparatus (FIG. 1). At the beginning of the test, 2 ml or the respective complex were injected into a dialytic hose with the defined molar mass exclusion limit of 100000 Dalton. The dialytic hose was clamped at both ends and was immersed in 1000 ml of isotonic sodium chloride solution (acceptor medium), brought to a temperature of 37° C. and moved at a defined agitation speed (300 rpm).

EXAMPLE 1

Testosterone Complex
   Complex 1:

| Testosterone | 1 part |
|---|---|
| Resomer RG 503 | 1 part |
| PE 2 | 8 parts |

Comparison of release against a suspension (reference) of the following composition:

| Testosterone | 1 part |
|---|---|
| Peanut oil | 9 parts |

FIG. 2 shows the percentage of testosterone released as a function of time. When the testosterone release from complex 1 and the reference was compared (FIG. 2), it became apparent that in both cases between 40% and 80% of active ingredient had been released after 38 days. Complex 1 was superior to the reference suspension as regards release delay.

EXAMPLE 2

Progesterone Complex
   Complex 2:

| Progesterone | 10 parts |
|---|---|
| Resomer L 104 | 5 parts |
| PE 1 | 85 parts |

FIG. 3 shows the percentage of progesterone released as a function of time. The release of progesterone from the complex according to the invention is delayed (FIG. 3). In this case about 4% of the progesterone had reached the acceptor medium after 24 hours. As the release profile is flattening, hormone release for up to 365 days can be assumed. This is in line with the slow biodegradation of the L 104 (Boehringer Ingelheim manufacturer's information) used.

EXAMPLE 3
Interleukin-2 Complex
Complex 3:

| | |
|---|---|
| Interleukin-2 | 10 parts |
| Resomer RG 503 H | 10 parts |
| PE 3 | 80 parts |

FIG. 4 shows the percentage of interleukin-2 released as a function of time. The release of interleukin-2 from the complex according to the invention is delayed (FIG. 4). In this case about 2% of the interleukin-2 had reached the acceptor medium after 24 hours. As the release profile is flattening, a long-term hormone release can be expected. This is in line with the slow biodegradation of the RG 503 (Boehringer Ingelheim manufacturer's information) used.

EXAMPLE 4
Testosterone Complex
Complex 4:

| | |
|---|---|
| Testosterone | 10 parts |
| Resomer RG 752 | 15 parts |
| PE 2 | 75 parts |

FIG. 5 shows the percentage of testosterone released as a function of time. The release of testosterone from the complex according to the invention is delayed (FIG. 5). In this case about 2% of the testosterone had reached the acceptor medium after 24 hours. As the release profile is flattening, a long-term hormone release can be expected. This is in line with the slow biodegradation of the RG 752 (Boehringer Ingelheim manufacturer's information) used.

Testing the Complex

The PE portion in the complex was determined gravimetrically. The following complexes were coagulated in an 0.9% NaCl solution:

| | | |
|---|---|---|
| 1) | Resomer ® RG 503 | 10 parts |
| | PE 2 | 90 parts, |
| 2) | Resomer ® L 104 | 15 parts |
| | PE 2 | 85 parts, |
| 3) | Resomer ® RG 752 | 20 parts |
| | PE 2 | 80 parts, |

Coagulate weight ($m_0$) was recorded. The coagulates were removed by filtration after 2 hours, 24 hours, and 7 days and immediately weighed ($m_{wet}$). The wet coagulate was dried to constant weight above silica gel in a vacuum and at room temperature ($m_{dry}$).

The mass balance of the wet coagulate was calculated as follows:

$$\text{Resomer content } (R\%): R\% = \frac{c \cdot m_0}{m_{wet}} \cdot 100\%$$

$$\text{Water content } (W\%): W\% = \frac{m_{wet} - m_{dry}}{m_{wet}} \cdot 100\%$$

PE content (P%): P%=100%−R%−W%
$m_o$ Weight of complex [g]
c Resomer concentration in the coagulate [g/g]
$m_{wet}$ Weight of the wet coagulate [g]
$m_{dry}$ Weight of the dried coagulate [g]

The composition of the dry coagulate of PE and polymer can be derived from the mass balances of the wet coagulates by outlining R% and P% at 100 parts (FIGS. 6–8).

Figure 1:
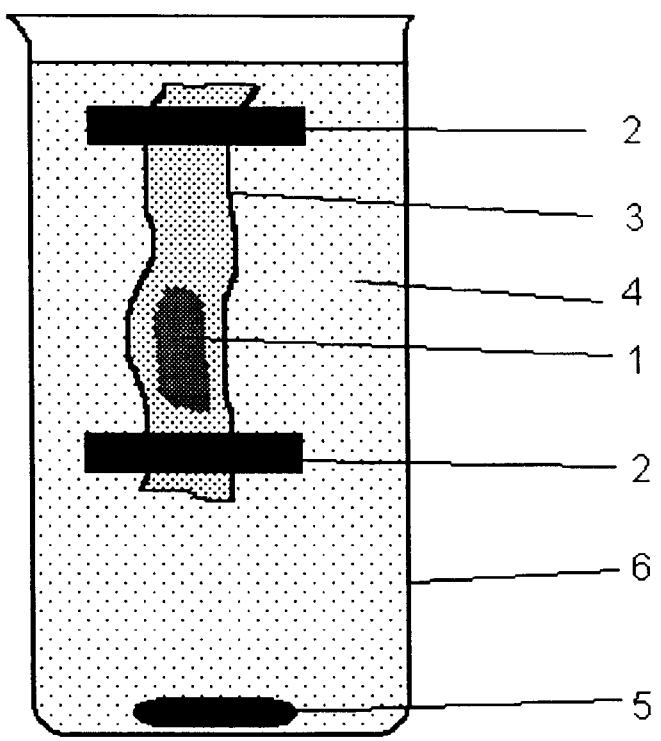
Figure 2:
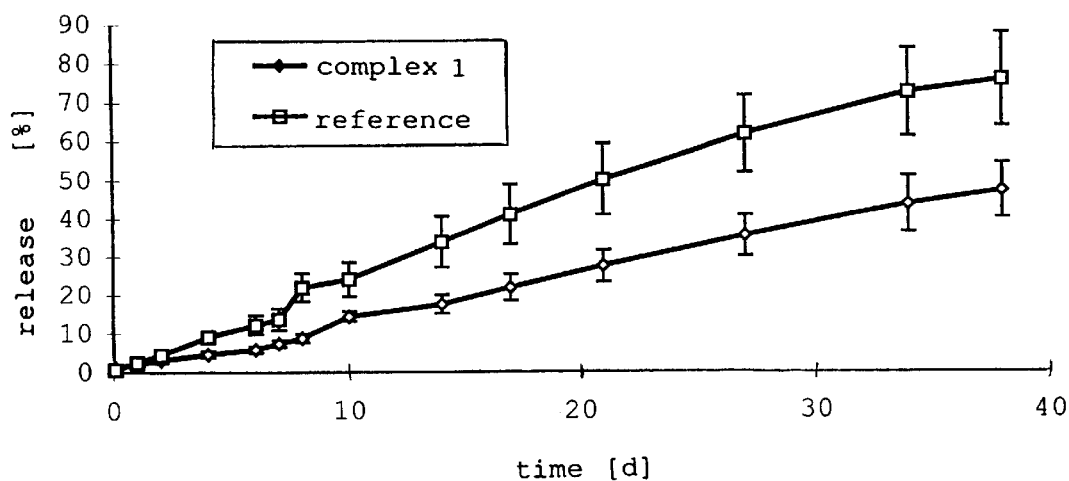
Figure 3:
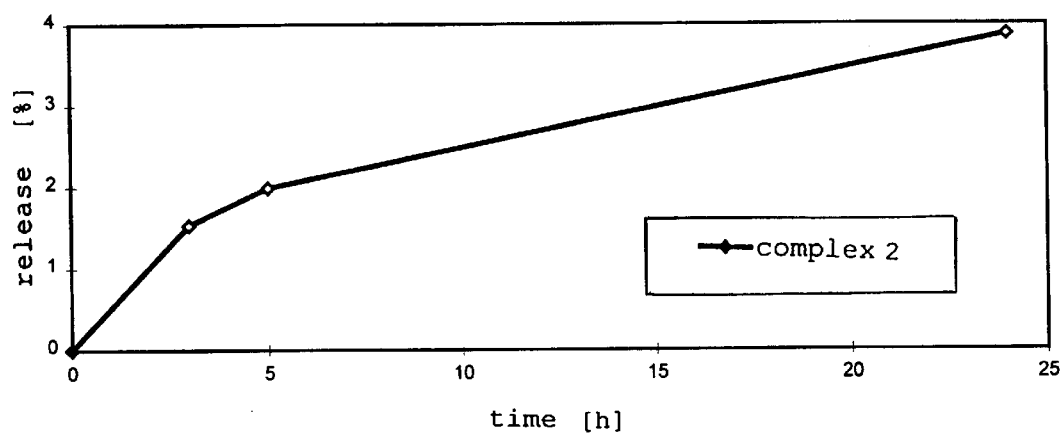
Figure 4:
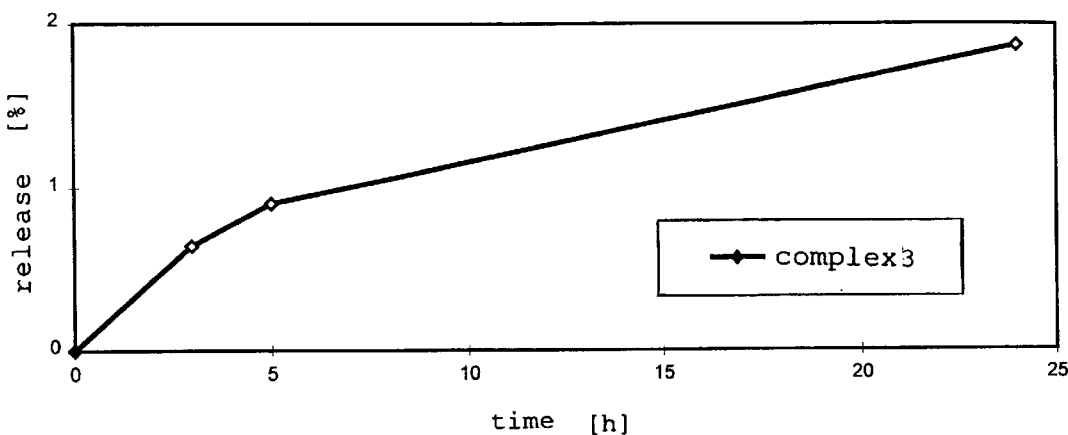
Figure 5:
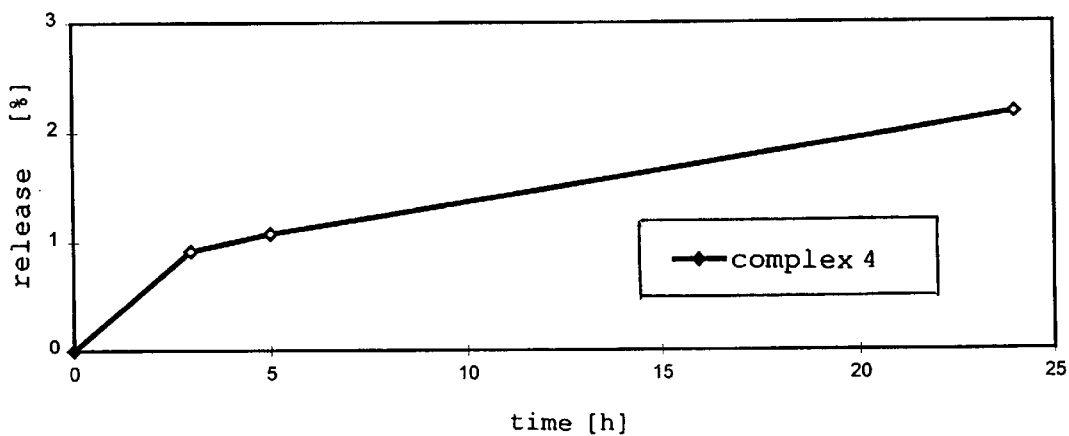
Figure 6:
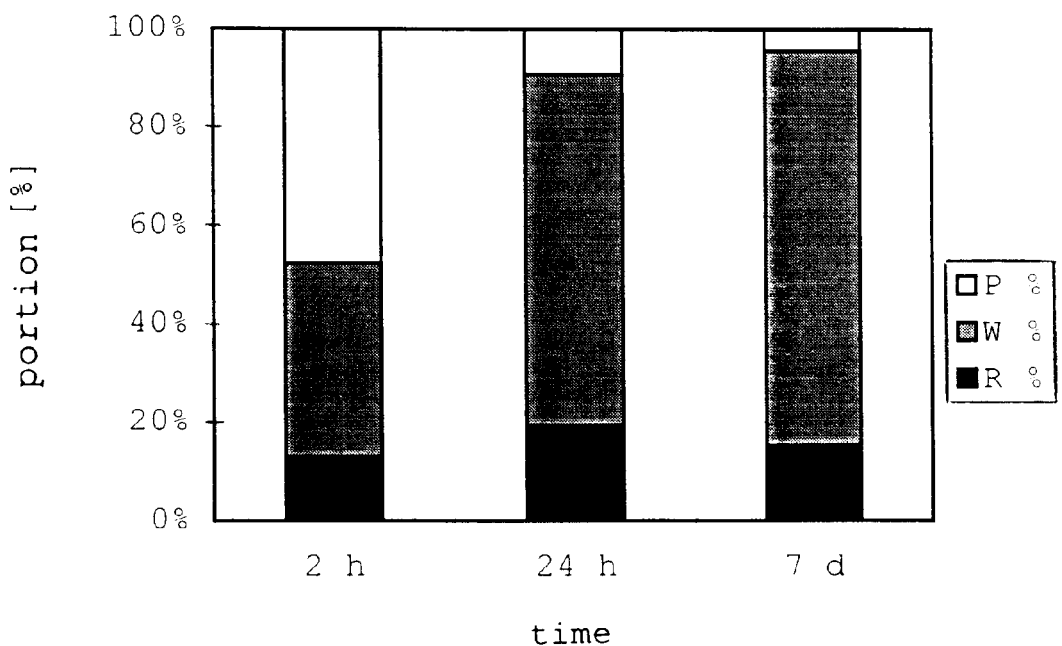
FIG. 6 shows the composition of the dry coagulate 1 as a function of time.
Figure 7:
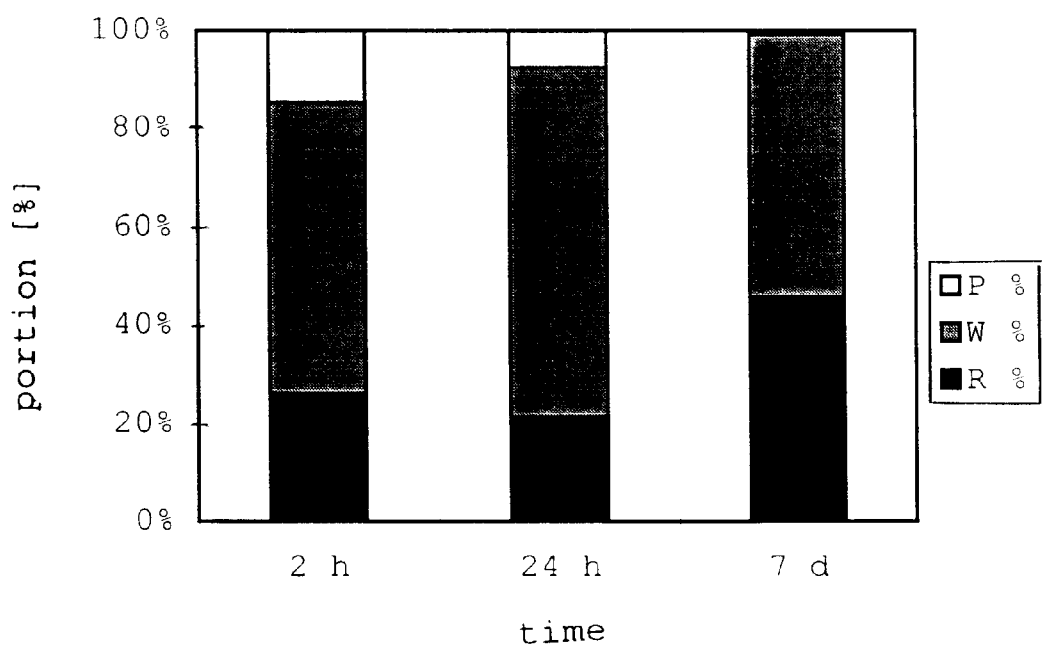
FIG. 7 shows the composition of the dry coagulate 2 as a function of time.
Figure 8:
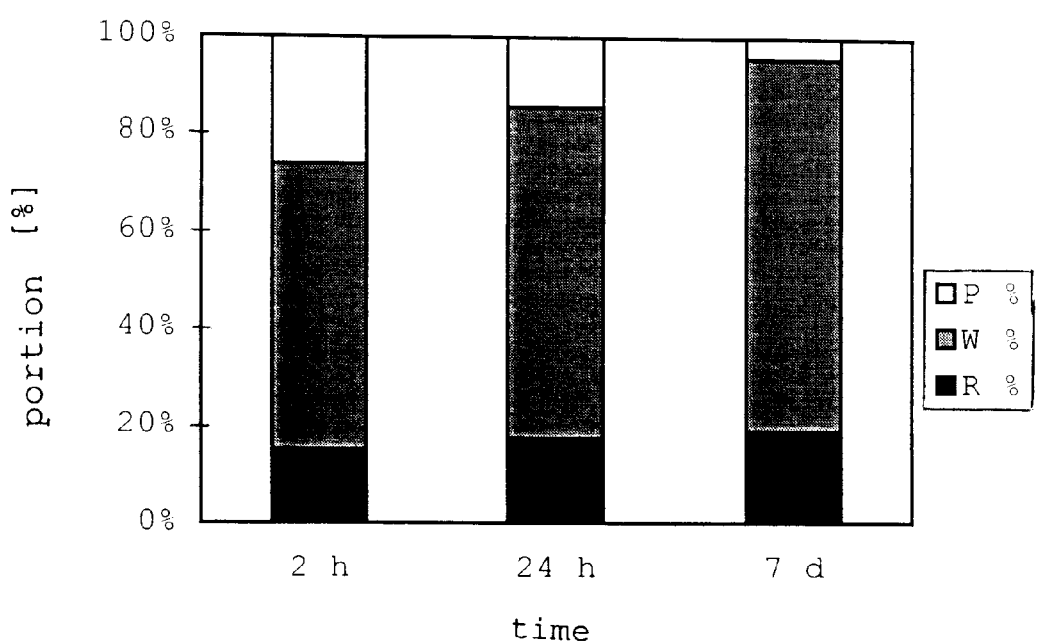
FIG. 8 shows the composition of the dry coagulate 3 as a function of time.

A defined portion of PE was detected in the dry coagulates in all cases (FIGS. 6, 7, 8). The PE portion in the dried coagulates is decreasing over time for all coagulates. Flushing of PE and coagulate biodegradation overlap.

LIST OF REFERENCE SYMBOLS

1 complex
2 locking clamps
3 dialytic hose
4 acceptor medium
5 magnetic stirrer
6 vessel

We claim:

1. An in-situ implant that can be produced by placing a sterile, injectable, and water-insoluble complex in a patient, the complex having a biodegradable polymer non-covalently bound to a biocompatible polyether with functional end-groups, the implant forming a coagulant on contact with a body fluid.

2. A method for producing an implant wherein a sterile injectable water-insoluble complex is formed by mixing together a biodegradable polymer and a biocompatible polyether wherein the biodegradable polymer and biocompatible polyether are not covalently bonded to each other but are capable of coagulation upon contact with a body fluid.

3. The method of claim 2 wherein the biodegradable polymer is mixed with a biocompatible polyether having functional end-groups.

4. A method for producing an injectable implant wherein a sterile injectable water-insoluble complex is formed by mixing together a biodegradable polymer and a biocompatible polyether having functional end-groups wherein the biodegradable polymer and biocompatible polyether are not covalently bonded to each other but are capable of coagulation upon contact with a body fluid.

5. A composition suitable for controlled release of a therapeutic agent in a patient, said composition comprising a water-insoluble injectable complex having a biodegradable polymer and a biocompatible polyether having functional end-groups, wherein the biodegradable polymer and biocompatible polyether are not covalently bonded to each other but are capable of coagulation upon injection into a patient to form a coagulant.

6. The composition according to claim 5 wherein the biodegradable polymer is a compound selected from the group of poly(α-hydroxy esters) or their copolyrners.

7. The composition according to claim 5 wherein the biocompatible polyether with functional end-groups is a compound of the general formula I

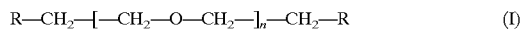

where
R represents —OH, —CH$_2$OH, —CH$_2$CH$_2$OH or their homologs, n is an integer from 4 to 12, and the relative molar mass of the compound of the general formula I is 200 to 600 Daltons.

8. The composition according to claim 7 wherein R represents —OH.

9. The composition according to claim 5 wherein the ratio of biodegradable polymer and polyether is in the range between about 1:100 and about 1:2.

10. The composition according to claim 9 wherein the ratio of biodegradable polymer and polyether is in the range between about 1:6 and about 1:3.

11. The composition according to claim 5 wherein the injectable complex further comprises a therapeutic agent selected from the group comprising hormones, immunomodulators, immunosuppressants, antibiotics, cytostatics, diruretics, gastro-intestinal agents, cardiovascular agents, anti-inflammatory agents, analgesics, local anaesthetics, and a neuropharmacological agent.

12. The composition according to claim 5 wherein the complex is sterile prior to use.

* * * * *